(12) United States Patent
Rolla et al.

(10) Patent No.: US 10,022,309 B2
(45) Date of Patent: Jul. 17, 2018

(54) COMPOSITION, COMPRISING HYDROFLUORIC ACID, FOR INHIBITING DENTAL EROSION

(71) Applicant: ZPEARPOINT AS, Jar (NO)

(72) Inventors: Gunnar Rolla, Oslo (NO); Per Stanley Thrane, Hvalstad (NO)

(73) Assignee: Zpearpoint AS (NO)

( * ) Notice: Subject to any disclaimer, the term of this patent is extended or adjusted under 35 U.S.C. 154(b) by 0 days.

(21) Appl. No.: 14/246,655

(22) Filed: Apr. 7, 2014

(65) Prior Publication Data

US 2014/0242000 A1    Aug. 28, 2014

Related U.S. Application Data

(62) Division of application No. 11/596,104, filed as application No. PCT/NO2005/000167 on May 18, 2005.

(30) Foreign Application Priority Data

May 14, 2004    (NO) .................................. 20042027

(51) Int. Cl.
| | | |
|---|---|---|
| *A61Q 11/00* | (2006.01) | |
| *A61K 8/21* | (2006.01) | |
| *A61K 8/02* | (2006.01) | |
| *A61K 8/00* | (2006.01) | |

(52) U.S. Cl.
CPC ................ *A61K 8/21* (2013.01); *A61Q 11/00* (2013.01)

(58) Field of Classification Search
CPC ............. A61K 11/00; A61K 8/00; A61K 8/21
USPC ....................................... 424/49, 52
See application file for complete search history.

(56) References Cited

U.S. PATENT DOCUMENTS

| | | | |
|---|---|---|---|
| 2,946,725 A | | 7/1970 | Norris et al. |
| 4,080,440 A | * | 3/1978 | DiGiulio et al. ............... 424/49 |
| 4,714,608 A | | 12/1987 | Rolla |
| 5,071,637 A | | 12/1991 | Pellico |
| 5,073,363 A | * | 12/1991 | Pellico ........................... 424/49 |
| 2003/0157145 A1 | | 8/2003 | Kalili et al. |

FOREIGN PATENT DOCUMENTS

| | | | |
|---|---|---|---|
| GB | 1 429 746 | * | 3/1976 |
| GB | 1450881 | * | 9/1976 |
| WO | 03/045344 | | 6/2003 |

OTHER PUBLICATIONS

Sorvari, R., et al. "Effect of Fluoride Varnish and Solution on Enamel Erosion in vitro." *Caries Res*(1994) vol. 28, pp. 227-232.
Hughes, J. A., et al. "The protective effect of fluoride treatments against enamel erosion in vitro." *Journal of Oral Rehabilitation* (2004) vol. 31, pp. 357-363.
van Rijkom, H., et al. "Erosion-inhibiting effect of sodium fluoride and titanium tetrafluoride treatment in vitro." *European Journal of Oral Sciences* (2003) vol. 111, pp. 253-257.
Examination report for corresponding EP application 05 750 454.0-2112.

\* cited by examiner

*Primary Examiner* — Lezah Roberts

(57) ABSTRACT

The present invention relates to a composition, for inhibiting dental erosion, and the use thereof. The composition comprises an aqueous solution of hydrofluoric acid, in which the concentration of hydrofluoric acid is 0.05%-2.00% and the pH is between 2.5 and 4.5.

11 Claims, 4 Drawing Sheets

COMPOSITION, COMPRISING HYDROFLUORIC ACID, FOR INHIBITING DENTAL EROSION

RELATED APPLICATIONS

This application is a divisional of copending application Ser. No. 11/596,104 filed on Sep. 11, 2008 which is a 371 of International Application PCT/NO2005/000167 filed on May 18, 2005, which designated the U.S., claims the benefit thereof. International Application PCT/NO2005/000167 designating the U.S., claims foreign priority from Norwegian Patent Application No.: 20042027 filed May 14, 2004 and incorporates the same by reference.

The present invention comprises a composition for inhibiting dental erosion, a process for preparing a composition for inhibiting dental erosion and use thereof.

BACKGROUND OF THE INVENTION

The present invention relates to oral compositions which contain fluoride in suitable concentrations. It has surprisingly been found that diluted hydrofluoric acid applied on dental hard tissues at pH 2.5-4.5 reduce their solubility to up to 90%, when these are subsequently exposed to erosive acids. The oral compositions of the present invention are thus formulated to reduce solubility of teeth and prevent or stop, development of dental erosions.

Dental erosions represent loss of dental hard tissues (enamel, dentine and cementum) presumably due to excessive consumption of acidic beverages, juices or fruits. In some cases concerning subjects with eating disturbances, strong acid from the stomach may reach the oral cavity and cause severe dental erosions. Food and beverages may contain or weak inorganic acids which may provide a pH as low as 3 or less, on the tooth surfaces, whereas the strong acid from the stomach may yield a pH at 1.5 or below.

Teeth are very strong and resistant against mechanical wear, but dissolves and lose their integrity at pH levels below pH 5.5. Dental erosions are related to dental caries, which also is caused by organic acids. However, in the case of caries the organic acids are formed in small amounts by bacteria located on the tooth surfaces (bacterial plaque) during metabolism of dietary carbohydrates, in particular sucrose.

The carious lesions formed are in areas which are usually covered with dental plaque (i.e. along the gingival margin, aproximally and in occlusal fissures. The caries process is progressing slowly and is caused by small amounts of acids. pH levels below 5.5 are known to cause cavities over time, and in dental cementum the "critical pH" is as high as pH 6. This is due to the chemical properties of cementum, which contains more carbonate than enamel, and thus has a higher solubility. The caries process produce cavities (i.e. localized loss of hard tissue underneath dental plaque, whereas dental erosions involve loss of hard dental tissue over whole surfaces. Dental erosions are caused by acids originating from the diet (or from the stomach) and involves most frequently the lingual and buccal aspects of the incisors, and the occlusal surfaces of molars, mainly the mandibular molars.

Dental caries was previously a major public health problem in the industrialized world. The use of fluoride prophylaxis, mainly in the form of fluorinated toothpaste, has improved the situation markedly, and dental caries is now mainly found in high risk groups, which constitute about 10% of the population in the industrialized world. Dental erosions are on the other side, found in large numbers of teenagers, that consume high amounts of acidic beverages. It appears that some individuals have higher resistance against these challenges than others, and all individuals with high consumption of acidic beverages do not contract dental erosions. Fluoride toothpaste and other conventional methods designed to stop dental caries, are not effective against dental erosions. The mechanism of the inhibition of caries by fluoride, is now well understood. It was originally thought that fluoride worked solely by reducing the solubility of enamel at the pH related to dental caries (pH 5.5-4.5). However, it is now realized that fluoride works mainly by re-mineralization. If fluoride ions are available in the plaque during a pH challenge in plaque, the calcium and phosphate released from the plaque become supersaturated with respect to fluorapatite (with contribution by the fluoride ions in plaque), and this solid phase is re-deposited on the tooth surface, thus eliminating the loss of mineral. However, this re-mineralization can only occur at pH above 4.5 and conventional fluoride methods are thus not effective concerning dental erosions which originate at pH levels below 4.5, as discussed above.

THE RELATED ART

In prior art fluoride methods are with few exception, designed as prophylaxis for dental caries. At a certain time it was believed that fluoride inhibited caries by reducing the solubility of dental enamel.

It has now been convincingly demonstrated that this is not an important aspect of the mechanism of fluoride in caries prophylaxis. It was shown that shark enamel, which consists of solid fluorapatite, was showing caries lesions when introduced in the human oral cavity, in, in situ experiments in high caries challenge regimen. Many experiments have been performed to reduce enamel solubility, usually at pH 4.5. Another frequently used experimental design was to measure acquisition of fluoride on the surface and in the depth of dental enamel. However, it was observed that no relationship existed between the acquisition of surface fluoride by a method, and its clinical effect (Murrey). It was reported that an acidulated phosphofluoride preparation was able to deposit high amounts of fluoride in the enamel surface, but no corresponding convincing improved caries inhibition was experienced, although some positive results were reported. However, no reference was given to a composition for inhibiting dental erosions. This problem was previously related to people (mostly farmhands) that worked on orange or lemon plantations and were supposed to eat large quantities of such fruits.

Stannous fluoride represents a special case. It was observed that stannous fluoride in toothpastes and in aqueous solution reduced the solubility of enamel at pH 4.5 (U.S. Pat. No. 2,946,725) and this was thought to be caused by the low pH of the toothpaste, which were due to stannous ions being hydrolized by formation, of SnOH and liberation of H+. Stannous pyrophosphate was added as an extra source of Sn++ ions. A claim of the patent above was that slightly soluble stannous compounds should be added to the toothpaste to obtain a pH between 3.5 and 6. No reference was made to dental erosions. Stannous fluoride toothpastes are still in use but they suffer from stability problems concerning both fluoride and stannous ions, and dental staining is a problem in even new and improved product (Perlich 1995).

In vitro studies showed that solutions of stannous fluoride showed decreasing pH upon storage, and that lowered pH reduced the solubility reduction of enamel (Muhler J. dent Res.). Büyükyilmaz et al. (1997) reported that pre-treatment of teeth with 1-4% aqueous solutions of titanium tetrafluoride inhibited the solubility of enamel in hydrochloric acid. The effect was suggested to be due to formation of a titanium containing "glaze" on the surface of the enamel. U.S. Pat. No. 5,004,597 represent an improvement where the stability of fluoride and stannous ions in toothpaste are improved. A stannous fluoride containing toothpaste which claims to be able to reduce the development of dental erosions (Solidox syreblokk), has recently been introduced on the Norwegian marked. However, stannous fluoride preparations have certain disadvantages; their shelf life are limited (due to oxidations of stannous ions), stannous fluoride is expensive, and dental stain is known to develop in some cases during long-term use of stannous fluoride. Titanium tetra fluoride is very expensive, and aqueous solutions exhibit a low pH and contain very high amounts of fluoride. None of these references disclosed teach a composition for inhibiting dental erosion and use thereof with diluted hydrofluoric acid of a pH between 2.5 and 4.5 as active agents against dental erosions.

NO 155225 B describes attempts to reduce the erosive potential of citric acid and citric acid containing beverages by adding fluoride to beverages.

Hughes, J. A. et al. "The protective effect of fluoride treatments against enamel erosion in vitro." J. of Oral Rehabilitation. 2004. 31; 357-363 describes the effect of addition of sodium fluoride to citric acid- or citric acid based drinks, on the erosion, and also by several commercial fluoride products. The authors found a slight effect by adding fluoride to citric acid or corresponding beverages, but these differences were not statistically significant. The acidulated gel which showed some beneficial effect on erosion, had a pH of 5.15, and can thus not relate to the present patent application. Citric acid with addition of fluoride was not significantly different from citric acid without fluoride (Table 3). The paper cites a paper by Larsen and Richards Caries Res 2002:

36-73: Fluoride is unable to reduce dental erosions from soft drinks. This paper supports the findings in D2. The present authors conclude in their discussion "differences in erosion between with and without fluoride were small and most did not achieve statistical significance"

Van Rijkom, H. et. al. "Erosion-inhibiting effect of sodium fluoride and titanium tetrafluoride treatment in vitro." Eur. J. Oral Sci. 2003.111; 253-257 concerns the erosive inhibiting effect of 1% neutral NaF treatment and a 4% solution of TiF4. Bovine teeth were pre-treated with either NaF or TiF4 and then exposed to 50 mM citric acid which contained calcium and phosphate and had a pH of 3. The results showed that the NaF reduced the mean lesion depth from 4.5 um to 3.5 um after 30 min of exposure, whereas TiF4 caused a reduction to 2.7 um. This is a moderate inhibition considering the mild erosion regime used. The differences were however statistically significant. TiF4 is an agent of academic interest, but it has no practical use due to a very high prize. The TiF4 is furthermore very hygroscopic and difficult to handle. Solutions of TiF4 have a pH of about 1.5.

Sorvari, R. et. al. "Effect of fluoride varnish and solution on enamel erosion in vitro." Caries Res. 1994. 28; 227-232 examine the effect of 24 h treatment with 1.2% NaF and of the commercial varnish Duraphat, on the hardness of enamel after subsequent exposure of the enamel samples by a cola-drink of pH 2.6 for 4 min. Both treatments improved the treatment compared with an untreated control. To expose teeth for 1.2% F— for 24 h is not a practical procedure, but is theoretical interesting. The effect should be seen in the light of the very light erosive power of a cola drink and the short exposure time.

U.S. Pat. No. 2,946,725 deals with toothpaste formulations concerning stannous fluoride-containing pastes and is thus not related to the present patent application. The pH of the pastes is also not relevant, as it relates to pH caused by hydrolysis of stannous ions and not by addition of diluted hydrofluoric acid.

SUMMARY OF INVENTION

Dental erosions are caused by acid-containing fruits and drinks. Traditional caries preventive measures including use of fluoride, are not effective against dental erosions. The invention involves use of diluted hydrofluoric acid, which is a weak acid with a pKa of 3.45. Pre-treatment of teeth with such acid in concentrations of 0.1-1%, has been shown to be able to protect tooth mineral against erosive acids. This effect is probably associated with the presence of un-dissociated HF which is abundant in aqueous solutions of hydrofluoric acids, in particular below the pKa of such acids.

Un-dissociated HF is thought to be able to get in contact with the mineralized tooth surface and thus get closer to this surface than any charged species of fluoride. It is thereby able to form erosion resistant products on the tooth surface which do not form in the absence of un-dissociated HF. This species is probably able to transfer fluoride to the mineral surface with a minimum of exposure free protons, which can cause damage to such surfaces. The invention can be used in product designed to enhance the resistance of teeth against erosive acids such as mouth rinses, gels and toothpastes.

The present invention is based on a new method by which the solubility of teeth is reduced and thus improved, beyond what is possible by use of the methods outlined above. It has now been discovered that diluted aqueous solutions of hydrofluoric acid reduces the solubility of dental of teeth against erosive acids, markedly, without having any of the disadvantages connected with the above methods.

The present invention comprises a composition for inhibiting dental erosion comprising aqueous solution of hydrofluoric acid in a concentration of 0.05%-2.00% with a pH between 2.5 and 4.5. The said composition comprises at least one of a humectant, a binder, a thickening agent, one or several abrasive agents, a liquid phase including a humectant, a surfactant and flavour. The abrasive agent is any one of silica, xerogels, hydrogels and aerogels. The abrasive agent is silica in a concentration of 3-75% by weight. The liquid phase of the present invention comprises said humectant in a concentration of 10-90% by weight of the composition. The humectant is chosen from cellulose, xanthan gum, sorbitol, glycerol, propylene glycol, polypropylene and polyethylene glycol. The binder and said thickening agent is any one of sodium carboxymethyl cellulose, hydroxyethyl cellulose, xanthan gum finely divided silica, Irish moss and synthetic hectorities in a concentration of 0.5-10% by weight of the composition. The composition comprises an anionic surfactant. A process for preparing a composition for inhibiting dental erosion comprising the steps of adding an aqueous solution of hydrofluoric acid in a concentration of 0.05-2.00% is also comprised in the present invention. The pH of the aqueous solution is between 2.5 and 4.5. The composition comprises at least one of a humectant, a binder, a thickening agent, one or several abrasive agents, a liquid phase including a humectant, a surfactant and flavour. Further, said abrasive agents is any one of silica, xerogels, hydrogels and aerogels, and said abrasive agent is silica in a concentration of 3%-75% by weight. The liquid phase according to the present invention, comprises said humectant in a concentration of 10-90% by weight of the composition. The humectant is chosen from cellulose, xanthan gum, sorbitol, glycerol, propylene glycol, polypropylene and polyethylene glycol. Further, the binder and said thickening agent is any one of sodium carboxymethyl cellulose, hydroxyethyl cellulose, xanthan gum finely divided silica, Irish moss and synthetic hectorities in a concentration of 0.5-10% by weight of the composition. The surfactant is an anionic surfactant.

The present invention describes use of a composition comprising aqueous solutions of hydrofluoric acid in a concentration of 0.05-2.00% for inhibiting dental erosion.

It has now been found that dental compositions consisting of diluted hydrofluoric acid pH 2.5-4.5 decrease the solubility of dental enamel in erosive acids (hydrochloric acid at pH 2.2 or citric acid pH 3.5) markedly (to 80% or more), even after a brief exposure of human teeth to the said compositions, before subsequent exposure to erosive acids. This shows that these compositions provide protection even against severe dental erosions caused by eating disorder whereby strong HCl may reach the oral cavity and the teeth. These compositions also protect against any organic or inorganic weak acids which may be present in beverages or fruits. The compositions include dentifrices, gels for topical application, lozenges and liquids. The maximum amounts of fluoride needed in the said compositions are the conventional concentrations used in such compositions, but dental hard tissues (enamel, dentine and cementum) are known to be highly soluble in erosive acids. The observations leading to the present invention were thus totally unexpected.

DETAILED DESCRIPTION

Figure 1:
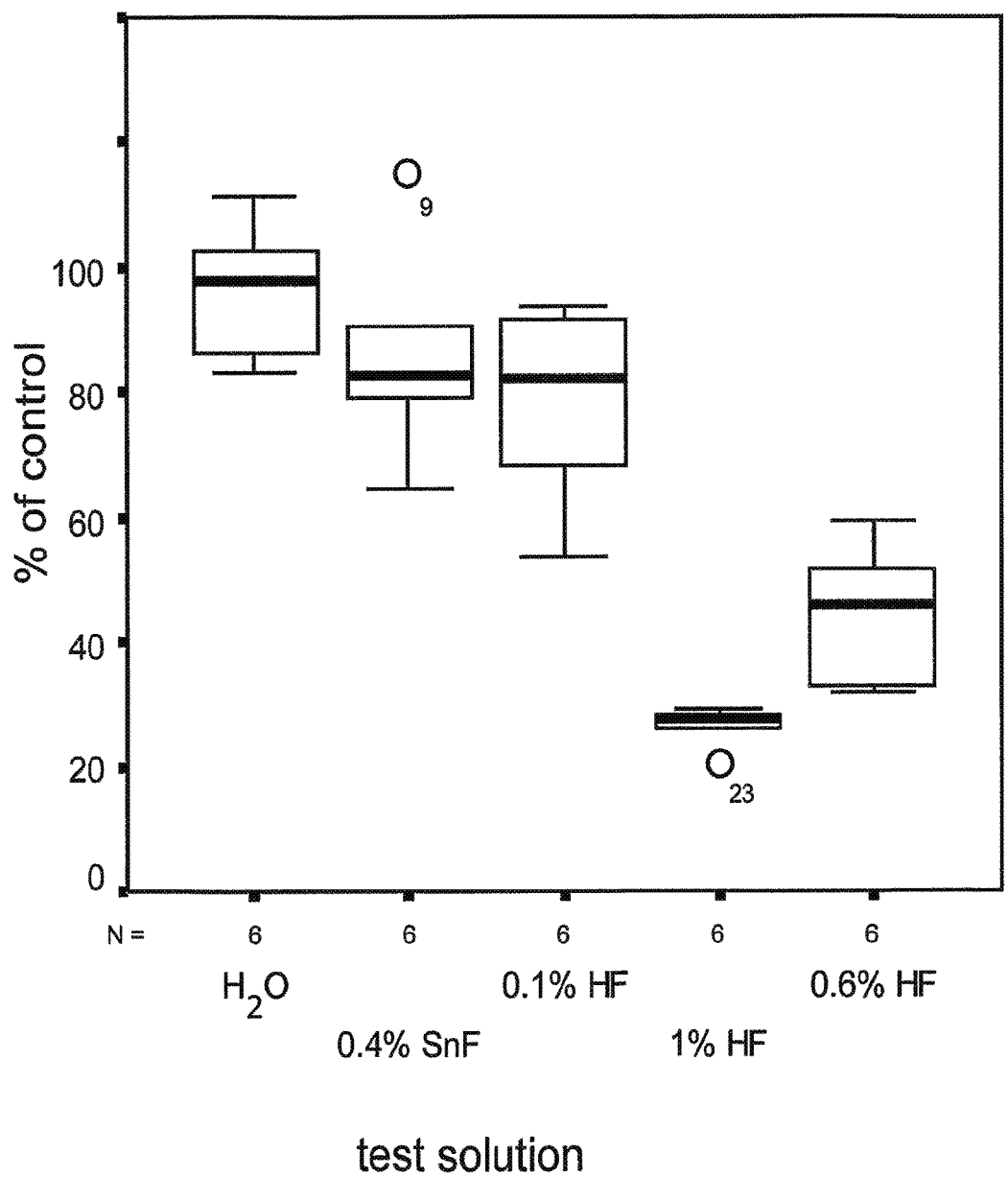
FIG. 1 describes solubility reduction of teeth in aqueous solutions.

Aqueous solutions of hydrofluoric acid (HF) are a weak acid which buffers between pH 3 and 4 and has a Pka of 3.45. The present invention is based on the observation that HF between pH3 and pH 4 has unique properties by providing dental mineral tissues (i.e. enamel dentine and cementum) with a surface layer which forms immediately, and protects the mineralized tissues against erosive acids. This layer consists of calcium fluoride-like material which is particularly resistant against erosive acids. Possibly because it is formed under acidic condition. In the experiments concerning this effect we have used severe erosive challenges to ascertain that this was a clinically significant effect. The erosive challenge was 0.1M citric acid of pH 2.2, for 30 min., and human teeth were used. In vivo it is known that human saliva can neutralize acids, and that proteins adsorbed to teeth will protect the dental surfaces to some degree, against erosive acids. No attempts to mimic these protective forces were included, and it is believed that the experimental conditions used are more severe than most clinical challenges.

Because of the buffering capacity of aqueous solutions of HF, the formation of the protective layer is formed at low pH, which appears to be favourable. It is furthermore believed that un-dissociated HF has the ability to come closer to the charged enamel surface than charged species of F. Un-dissociated HF can probably interact with the tooth surface by ionic exchange without, (or with a minimum of), free protons, which could etch and cause damage to the tooth surface. This concept would indicate that the region below the Pka is of particular significance for the unique effect of aqueous HF.

The oral compositions of the present invention may contain orally acceptable ingredients in conventional amounts, depending upon the final form of the composition, i.e. whether a dentifrice, a gel or a lozenge. A dentifrice will usually comprise an abrasive agent cleaning agent in an amount of from 3-75% by weight. Suitable abrasive cleaning agents are particulate aluminas, silica, xerogels, hydrogels and aerogels, and precipitated particulate silicas, calcium pyrophosphate, insoluble sodium metaphosphate, calcium carbonate, dicalcium orthophosphate and several others.

Dentifrices usually contain liquid phase comprising water and humectants in amounts of 10-99% by weight. Typical humectants are sorbitol, glycerol, propylene glycol, polypropylene glycol and many others.

A wide variety of thickening agents or binders are used in dentifrices including sodium carboxyl methyl cellulose, hydroxyethyl cellulose, finely devided silica, xanthan gum, Irish moss and synthetic hectorites. The amount of binders will usually range from 0.5-10% by weight of the dentifrice.

A further conventional ingredient of a dentifrice is an organic surfactant. Anionic surfactant is usually preferred because of their good foaming properties. Sodium lauryl sulphate is usually chosen, but an alkyl aryl sulphates, especially sodium dodecyl benzene sulphonate can be used in the present invention.

Various optional ingredient may be included of the invention including flavouring agents, sweetening agent such as sodium saccharin, and whitening agent such as titanium dioxide, anti-plaque agents, and agents for adjusting the pH of the dentifrice, which may range from 2.8-4.5. Such agents for acidification includes citric-, acetic- or maleic acids and their buffers. Weak inorganic acids such as phosphoric or fluoride acids, and strong acids as hydrochloric acid and its buffers.

A gel for topical application according to the present invention may contain from 1% to 0.1% F, depending on whether the gel is designed for weekly or daily use. The gel contain a thickening agent such as water soluble salts such as sodium carboxy methyl cellulose. Natural gums like gum arabic can also been used as thickeners in gels. The concentration of thickener is usually from 1-2%. A sweetening agent like xylitol or saccharin can be added in amounts of 5-10% or 0.2-0.3%, respectively, and a flavouring agent.

A lozenge according to the present invention should contain 0.25 mg F$^-$ and 100 mg of citric acid, and in addition 400 mg of xylitol, a flavouring agent and necessary constituents up to 0.6 g.

EXPERIMENT

Figure 2:
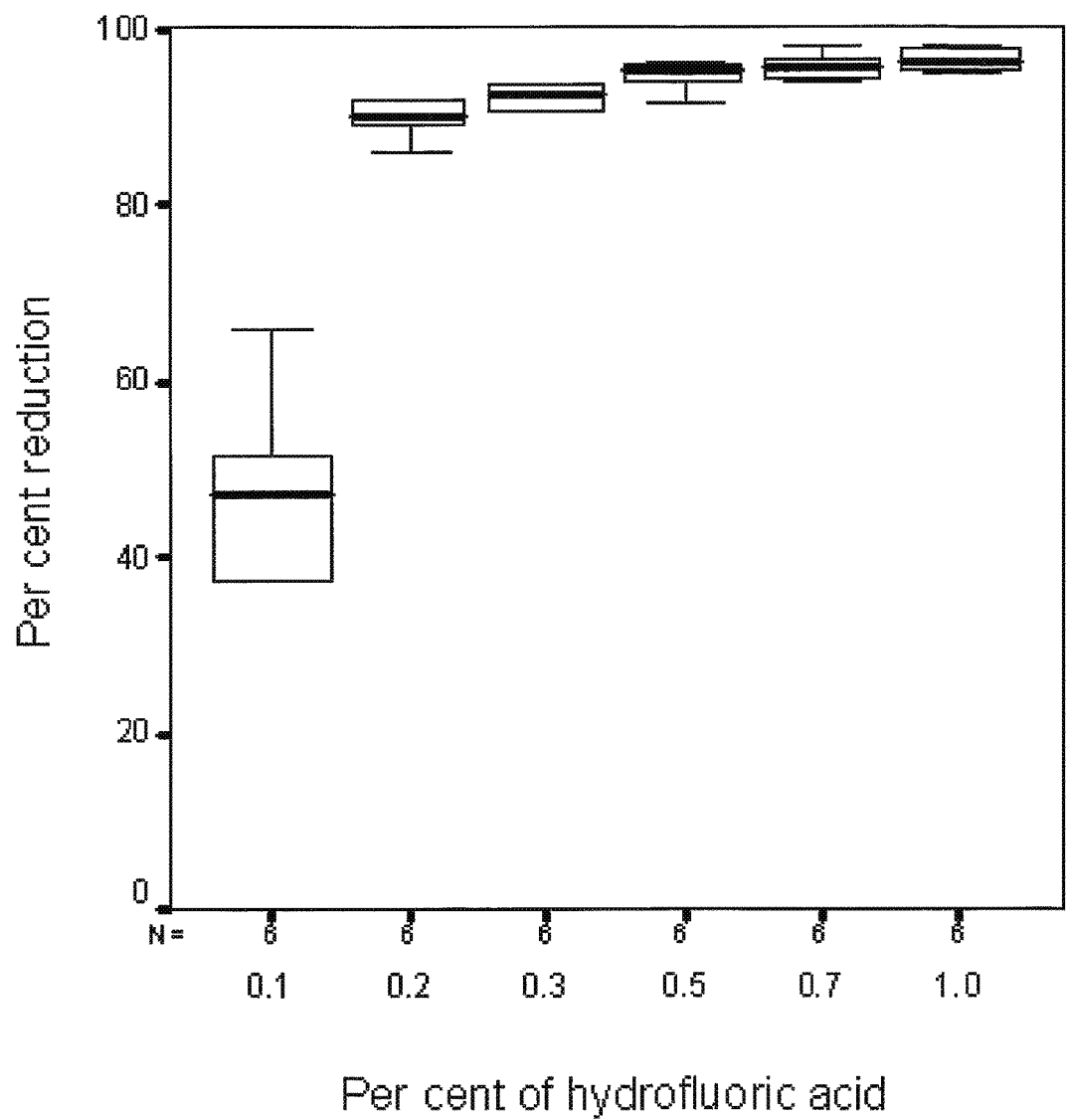
FIG. 2 describes solubility reduction of enamel.
Figure 3:
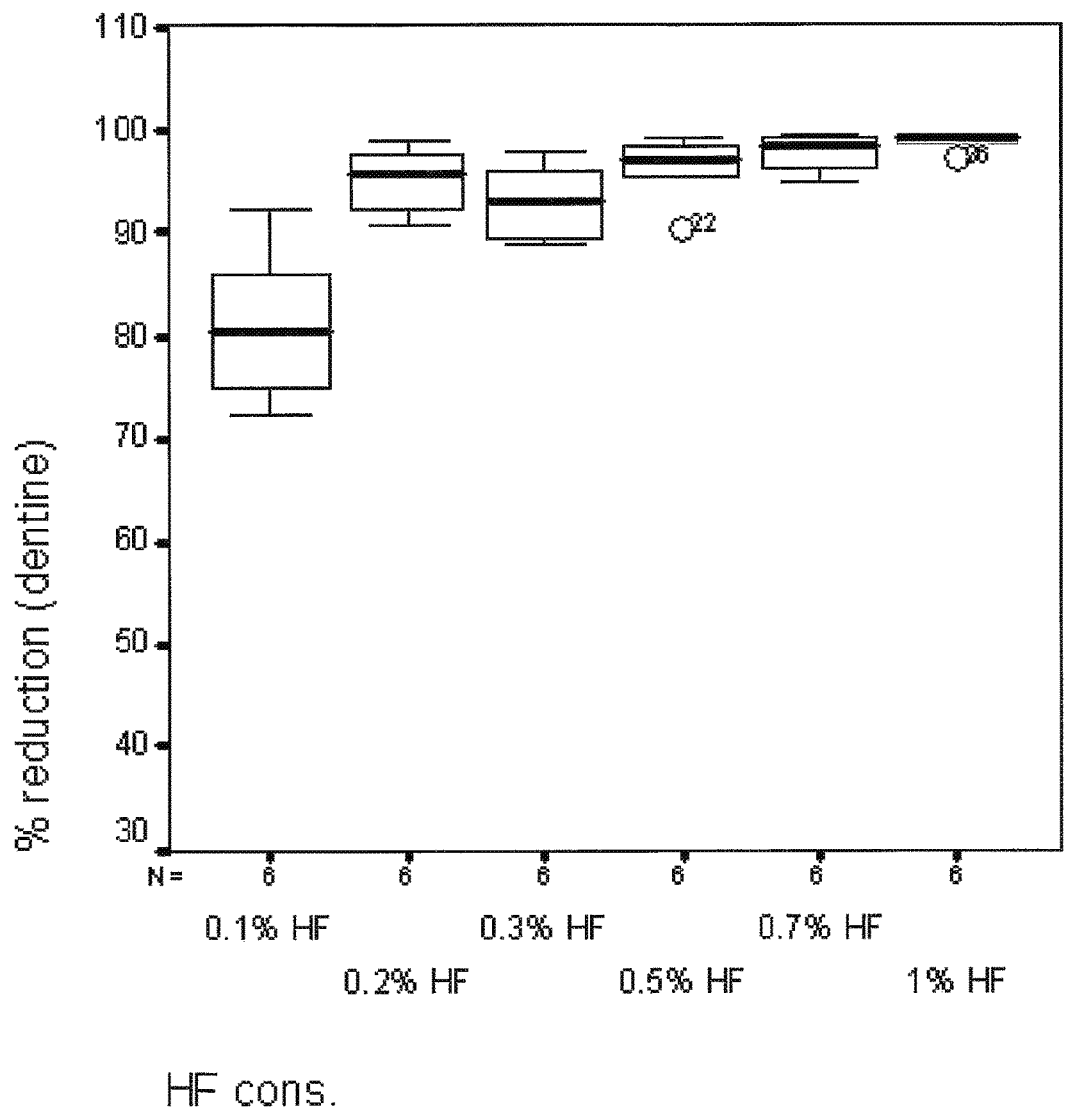
FIG. 3 describes solubility reduction of dentine.
Figure 4:
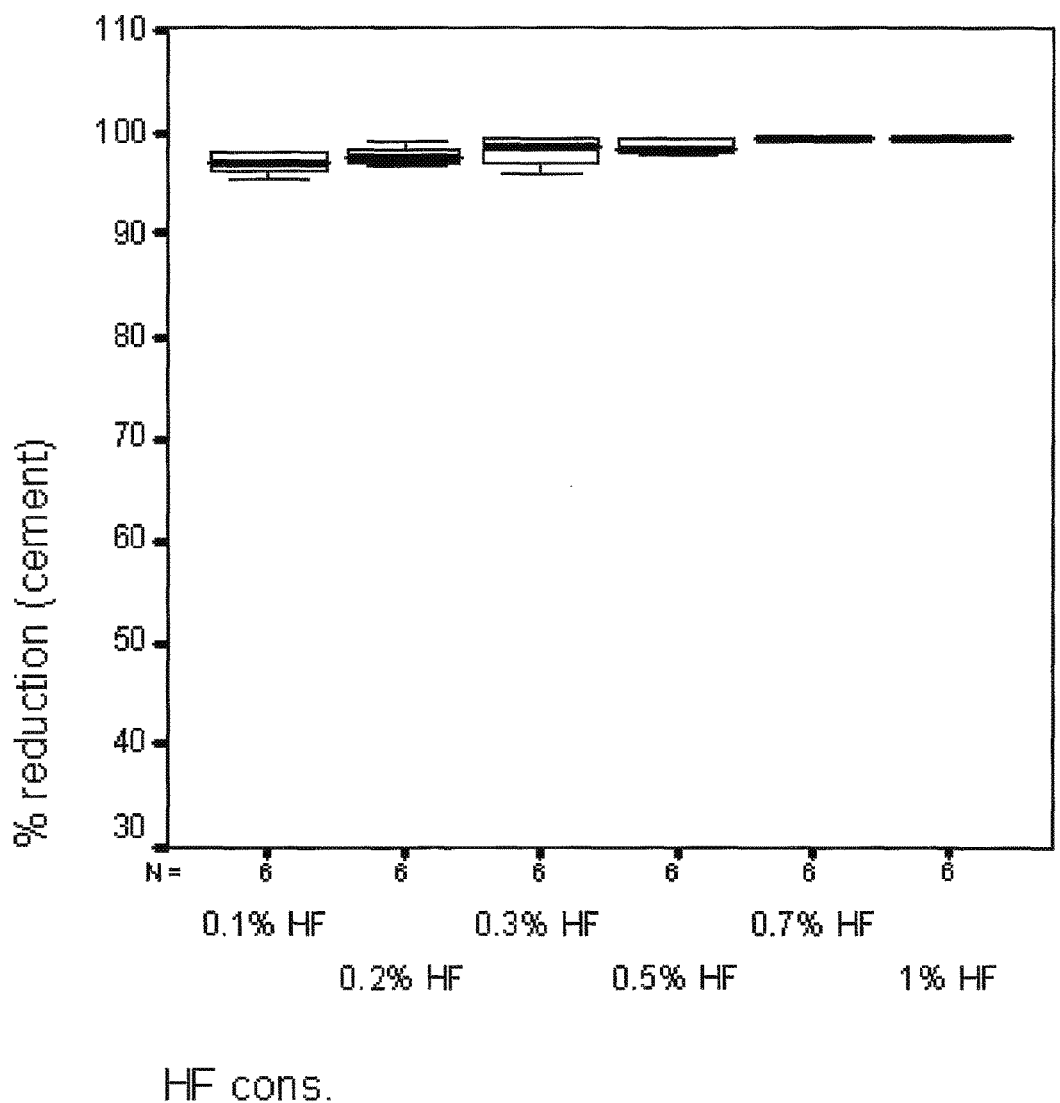
FIG. 4 describes solubility reduction of cementum.

Extracted teeth were cleaned and pre-treated for 5 min with 0.01% HCl to eliminate differences in solubility between the individual teeth, and then treated with diluted hydrofluoric acid. The teeth (usually 6 parallels) were then exposed to 0.1M citric acid or 0.01% HCl for 30 min, and the release of calcium into the acid measured by atomic absorption. The teeth treated with hydrofluoric acid were compared with control teeth (usually 6) which were only exposed to water. The results are given in FIG. 1. It can be seen that treatment, with 0.1% hydrofluoric acid gave a solubility reduction of 20% of the control, whereas 1% hydrofluoric acid gave a solubility reduction of close to 80%. Teeth treated with 0.4% of stannous fluoride was included for comparison. FIG. 1 shows the results of whole teeth treated with 0.01M HCl, whereas FIGS. 2, 3 and 4 shows the result of etching with 0.1% citric acid on enamel, dentine and cementum. Treatment with low concentrations of aqueous solutions of HF cause major reductions in solubility of the tooth samples. This example demonstrates that diluted hydrofluoric acid (0.1-1.0%) reduces the solubility of enamel (see FIG. 2), Dentine (see FIG. 3) and cementum (see FIG. 4) in 0.1M citric acid.

The teeth were cut in two at the enamel cementum junction and the exposed dentine covered by acid resistant varnish. Dentin samples was made by removing enamel from tooth crowns and varnished as described above. The experiments were performed in 6 parallels. The tooth samples were first exposed to 0.1M citric acid for 30 min. The teeth were then washed in distilled water and dried, and then treated with the respective dilutions of hydrofluoric acid for 10 min. The teeth were individually treated and each tooth served as its own control. The teeth were again washed and dried and then treated with 0.1M citric acid for the second time.

The solubility of the tooth samples was assessed by measuring the concentration of calcium in the citric acid. A reduction in calcium concentration between the first and second citric acid samples was assumed to be caused by the profylactic treatment with hydrofluoric acid dilutions.

It can be seen from the figures that 0.1% of HF caused about 45% reduction in the solubility of enamel (FIG. 2), 80% reduction in dentine solubility (FIG. 3), and 95% reduction of cementum solubility (FIG. 4). 0.2% HF reduced the solubility 90%, 90% and 95% respectively.

It can thus be seen that very low concentrations of HF have major effects on solubility. (0.1% HF represents 1 part of 40% HF in 399 parts of water and its application on teeth represents no health hazard.

Example 1

A gel having the following composition was made:

| Ingredient | % |
| --- | --- |
| Silica thickener | 50% |
| Xanthan gum | 0.1% |
| Sodium saccharin | 0.23% |
| Xylitol | 5% |
| Cardemom oil | 1% |
| Hydrofluoric acid | 0.3% |
| Water ad | 100% |

Example 2

A dentifrice having the following composition was made:

| Silica abrasive | 60% |
| --- | --- |
| Sorbitol syrup (70% sol) | 25% |
| Xanthan gum | 1% |
| Sodium saccharide | 0.25% |
| Sodium lauryl sulfate | 1.0% |
| Flavour (Cardedmom oil) | 1.0% |
| Hydrofluoric acid | 0.1% |
| Water ad | 100% |

Example 3

A toothpaste according to the present invention (%)
Silica Abrasives: 56
Sorbitol (70% sol): 21
Sodium lauryl sulphate: 1.5
Xanthan gum: 0.875
Titan dioxide: 0.5
HCl . . . (37%): 0.15
F—: 0.15%
Citric buffer pH 3.0, 0.1M ad 100

REFERENCES

Muffler et al.: J. dent Res. 1952:31:756-60
Ellingsen et al. Scand. J. dentres. 1982:90:9-13
Perlich et al. J. Clin. dent. 1995, VI:54-58
White: J. Clin. dent. 1995, VI: 29-36.
Rolla and Saxegaard: Jdent. Res 1990 69: 412-418
Rolla: Acta Odontol. Scand. 1988:46 341-345.
Brudevold et al, J. det. Res 1967, 37 Sn kan redusere F opptak
Murrey: Fluorides in caries prevention, Wright and Sons ltd 1976 p 129.
Büyükylmaz et al. Eur J Oral Sci 1997:105: 473-77
Crisp Practitioner 1974; 212: 525-35
Miles et al. J Can Dent Ass 1985; 10: 750-60
Levinson N Y J Dent 1986; 56: 90-4
Gilmore et al. Brit. Dent J 1993; 175:368-72
Meurman et al. Oral Surg Oral Med Oral Pathol 1994; 78: 583-9
Meurman and Frank; Caries Res 1991; 25:1-6

PATENTS

Rolla et al U.S. Pat. No. 5,096,702 5/1992
Norris er al. U.S. Pat. No. 2,946,725 7/1960
Grigor et al. U.S. Pat. No. 5,833,925 11/199

The invention claimed is:

1. A method for inhibiting dental erosion in a subject, comprising:
   administering to teeth of the subject an aqueous composition that consists essentially of un-dissociated hydrofluoric acid (HF), water and at least one of a humectant, a binder, a thickening agent, an abrasive agent, a surfactant and a flavor;
   wherein the HF is present in an aqueous concentration of 0.1-1% (w/v) and a pH of the aqueous composition is between 2.5 and 4.5.

2. The method according to claim 1, wherein the abrasive agent is selected from the group consisting of silica, xerogels, hydrogels, aerogels and mixtures thereof.

3. The method according to claim 2, wherein said abrasive agent is silica present in the composition in a concentration of 3-75% by weight.

4. The method according to claim 1, wherein the composition comprises a liquid phase and said liquid phase comprises said humectant in a concentration of 10-90% by weight of the composition.

5. The method according to claim 1, wherein said humectant is selected from the group consisting of cellulose, xanthan gum, sorbitol, glycerol, propylene glycol, polypropylene and polyethylene glycol.

6. The method according to claim 1, wherein said binder and said thickening agent is any one of sodium carboxymethyl cellulose, hydroxyethyl cellulose, xanthan gum finely divided silica, Irish moss and synthetic hectorites in a concentration of 0.5-10% by weight of the composition.

7. The method according to claim 1, wherein said surfactant is an anionic surfactant.

8. A method for inhibiting dental erosion in a subject, comprising:

administering to teeth of the subject an aqueous composition comprising un-dissociated hydrofluoric acid (HF), wherein the un-dissociated HF is present in an aqueous concentration of 0.1-1% (w/v) and a pH of the aqueous composition is between 2.5 and 4.5, and wherein the aqueous composition is administered in the form of a gel.

9. The method according to claim 1, wherein said aqueous composition comprises the humectant, the binder, the thickening agent, the abrasive agent, the surfactant and the flavor.

10. A method for inhibiting dental erosion in a subject, comprising:

administering to teeth of the subject an aqueous composition comprising un-dissociated hydrofluoric acid (HF), wherein the un-dissociated HF is present in an aqueous concentration of 0.1-1% (w/v) and a pH of the aqueous composition is between 2.5 and 4.5, and wherein the aqueous composition is administered in the form of a dentifrice.

11. A method for inhibiting dental erosion in a subject, comprising:

administering to teeth of the subject an aqueous composition comprising un-dissociated hydrofluoric acid (HF), wherein the un-dissociated HF is present in an aqueous concentration of 0.1-1% (w/v) and a pH of the aqueous composition is between 2.5 and 4.5, and wherein the aqueous composition further comprises at least one selected from the group consisting of a humectant, a binder, a thickening agent, an abrasive agent, a surfactant, an abrasive agent and a flavoring agent.

* * * * *